(12) United States Patent
Nelson (10) Patent No.: US 7,998,200 B2
(45) Date of Patent: Aug. 16, 2011

(54) VOICE PROSTHESIS DEVICE

(75) Inventor: Jesse N. Nelson, Oxnard, CA (US)

(73) Assignee: Helix Medical, LLC, Plymouth, MI (US)

( * ) Notice: Subject to any disclaimer, the term of this patent is extended or adjusted under 35 U.S.C. 154(b) by 1163 days.

(21) Appl. No.: 11/145,791

(22) Filed: Jun. 6, 2005

(65) Prior Publication Data

US 2006/0276893 A1    Dec. 7, 2006

(51) Int. Cl.
*A61F 2/20* (2006.01)

(52) U.S. Cl. .......................................................... 623/9

(58) Field of Classification Search ........... 623/9, 26.68, 623/1.15
See application file for complete search history.

(56) References Cited

U.S. PATENT DOCUMENTS

| | | | |
|---|---|---|---|
| 3,137,299 A | 6/1964 | Tabor | |
| 4,304,228 A * | 12/1981 | Depel | 128/200.26 |
| 4,325,366 A * | 4/1982 | Tabor | 128/207.16 |
| 4,435,853 A | 3/1984 | Blom et al. | |
| 4,582,058 A * | 4/1986 | Depel et al. | 128/207.17 |
| 4,586,931 A | 5/1986 | Blom et al. | |
| 4,596,248 A | 6/1986 | Lieberman | |
| 4,596,579 A | 6/1986 | Pruitt | |
| 4,610,691 A | 9/1986 | Depel et al. | |
| 4,614,516 A | 9/1986 | Blom et al. | |
| 4,773,412 A | 9/1988 | Blom | |
| 4,808,183 A | 2/1989 | Panje | |
| 4,820,304 A * | 4/1989 | Depel et al. | 623/9 |
| 4,911,716 A * | 3/1990 | Blom et al. | 623/9 |
| 5,027,812 A | 7/1991 | Shapiro et al. | |
| 5,059,208 A * | 10/1991 | Coe et al. | 623/9 |
| 5,064,433 A | 11/1991 | Blom et al. | |
| 5,300,119 A | 4/1994 | Blom | |
| 5,314,470 A | 5/1994 | Persson | |
| 5,480,432 A * | 1/1996 | Suding et al. | 623/9 |
| 5,507,809 A * | 4/1996 | Blom | 623/9 |
| 5,571,180 A | 11/1996 | Blom | |
| 5,578,083 A * | 11/1996 | Laguette et al. | 623/9 |
| 5,632,775 A * | 5/1997 | Suding et al. | 623/9 |
| 5,693,097 A | 12/1997 | Laguette et al. | |
| 5,738,095 A | 4/1998 | Persson | |
| 5,919,231 A | 7/1999 | Blom et al. | |
| 5,957,978 A | 9/1999 | Blom | |
| 5,976,151 A | 11/1999 | Siegbahn | |
| 6,422,235 B1 | 7/2002 | Persson | |
| 6,484,345 B2 | 11/2002 | Seder et al. | |

(Continued)

FOREIGN PATENT DOCUMENTS

FR    2 494 581 A1    5/1982

(Continued)

*Primary Examiner* — Corrine M McDermott
*Assistant Examiner* — Christopher D Prone
(74) *Attorney, Agent, or Firm* — Ronald W. Wangerow, Esq.; Harness, Dickey & Pierce, P.L.C.

(57) ABSTRACT

A voice prosthesis device includes a barrel defining a passageway, a tracheal flange adjacent a tracheal end of the barrel and an esophageal flange adjacent an esophageal end of the barrel. The passageway includes a first stop extending inwardly from a sidewall of the passageway between the tracheal and esophageal ends and a plurality of second stops extending inwardly from the sidewall of the passageway between the first stop and the esophageal end of the passageway. A valve mechanism is located between the first and second stops and permits flow through the passageway from the tracheal end and impedes flow through the passageway from the esophageal end.

19 Claims, 11 Drawing Sheets

U.S. PATENT DOCUMENTS

| | | |
|---|---|---|
| 6,722,367 B1 | 4/2004 | Blom |
| 6,772,758 B2 | 8/2004 | Lambert |
| 6,776,797 B1 | 8/2004 | Blom et al. |
| 6,948,526 B2 * | 9/2005 | Seder et al. .................. 137/855 |
| 2002/0193879 A1 * | 12/2002 | Seder et al. ...................... 623/9 |
| 2005/0171602 A1 * | 8/2005 | Goldberg et al. ................ 623/9 |

FOREIGN PATENT DOCUMENTS

| | | |
|---|---|---|
| WO | 96/36386 | 11/1996 |
| WO | 02/083031 A2 | 10/2002 |
| WO | 03/057082 A | 7/2003 |
| WO | WO 03/057082 A1 | 7/2003 |

* cited by examiner

VOICE PROSTHESIS DEVICE

FIELD OF THE INVENTION

This invention relates to voice restoration, and specifically to certain types of devices, hereinafter sometimes, voice prosthesis devices, which are sometimes used in voice restoration.

BACKGROUND OF THE INVENTION

Various types of voice prosthesis devices are known. There are, for example, the devices illustrated and described in U.S. Pat. Nos. 3,137,299; 4,304,228; 4,325,366; 4,435,853; 4,582,058; 4,586,931; 4,610,691; 4,614,516; 4,773,412; 4,808,183; 4,820,304; 4,911,716; 5,027,812; 5,059,208; 5,064,433; 5,300,119; 5,314,470; 5,480,432; 5,507,809; 5,571,180; 5,578,083; 5,632,775; 5,693,097; 5,738,095; 5,919,231; 5,957,978; 5,976,151; 6,422,235; 6,484,345; 6,722,367; 6,772,758; and, 6,776,797; and published PCT application WO 03/057082. The disclosures of these references are hereby incorporated herein by reference. This listing is not intended to be a representation that a complete search of all relevant art has been made, or that no more pertinent art than that listed exists, or that the listed art is material to patentability. Nor should any such representation be inferred.

DISCLOSURE OF THE INVENTION

According to an aspect of the invention, a voice prosthesis device for insertion into a tracheoesophageal opening of a wearer comprises a barrel providing a passageway therethrough, a tracheal flange adjacent a tracheal end of the barrel and an esophageal flange adjacent an esophageal end of the barrel. The tracheal flange and esophageal flange aid in retaining the voice prosthesis device in the tracheoesophageal opening. The passageway includes a first stop extending inwardly from a sidewall of the passageway between the tracheal and esophageal ends and a plurality of second stops extending inwardly from the sidewall of the passageway between the first stop and the esophageal end of the passageway. A valve mechanism between the first stop and the second stops permits flow through the passageway from the tracheal end and impedes flow through the passageway from the esophageal end.

Illustratively according to this aspect of the invention, the passageway includes an axis about which it is generally symmetric. The multiple second stops extend generally radially inwardly from the sidewall toward the axis Further illustratively according to this aspect of the invention, the multiple second stops are perimetrally substantially uniformly spaced about the sidewall.

Additionally illustratively according to this aspect of the invention, the passageway adjacent the tracheal end of passageway has a smaller transverse dimension than a transverse dimension of the passageway adjacent the esophageal end thereof.

Illustratively according to this aspect of the invention; the first stop is formed at a junction between the sidewall adjacent the tracheal end of the passageway and the sidewall adjacent the esophageal end of the passageway.

Further illustratively according to this aspect of the invention, the first stop is provided adjacent the tracheal end of the passageway.

Illustratively according to this aspect of the invention, the valve mechanism comprises a cartridge providing a valve seat, a valve closure, and means for mounting the valve closure for movement between the valve seat, where the closure impedes flow through the passageway from the esophageal end, and positions away from the valve seat, where the closure permits flow through the passageway from the tracheal end.

Further illustratively according to this aspect of the invention, the valve closure and the means for mounting the valve closure for movement between the valve seat and positions away from the valve seat are unitarily formed from a resilient elastomer.

Additionally illustratively according to this aspect of the invention, the means for mounting the valve closure for movement between the valve seat and positions away from the valve seat comprises an elastomeric ring and an elastomeric hinge element having a first end formed on the elastomeric ring. The valve closure is formed on a second end of the elastomeric hinge element. The cartridge accommodates the elastomeric ring and elastomeric hinge element.

Illustratively according to this aspect of the invention, the cartridge comprises a groove opening radially outwardly from an axis of the voice prosthesis for accommodating the elastomeric ring and a notch opening toward one of a tracheal end and an esophageal end of the cartridge for accommodating the elastomeric hinge element.

Further illustratively according to this aspect of the invention, the notch opens toward the esophageal end of the cartridge.

Additionally illustratively according to this aspect of the invention, the resilient elastomer further comprises an antimicrobial.

Illustratively according to this aspect of the invention, the antimicrobial comprises a metal atom or ion. Illustratively, the antimicrobial comprises silver oxide powder.

According to another aspect of the invention, a method is provided for making a voice prosthesis device for insertion into a tracheoesophageal opening of a wearer. The method includes forming a barrel providing a passageway therethrough, forming adjacent a tracheal end of the barrel a tracheal flange, and forming adjacent an esophageal end of the barrel an esophageal flange. The method further includes forming in the passageway a first stop extending inwardly from a sidewall of the passageway between the tracheal and esophageal ends and forming in the passageway a plurality of second stops extending inwardly from the sidewall of the passageway between the first stop and the esophageal end of the passageway. The method further includes inserting between the first stop and the plurality of second stops a valve mechanism permitting flow through the passageway from the tracheal end and impeding flow through the passageway from the esophageal end.

Illustratively according to this aspect of the invention, forming in the passageway a plurality of second stops comprises forming in the passageway a plurality of second stops perimetrally substantially uniformly spaced about the sidewall.

Illustratively according to this aspect of the invention, inserting between the first stop and the plurality of second stops a valve mechanism comprises inserting between the first stop and the plurality of second stops a cartridge, providing in the cartridge a valve seat, providing in the cartridge a valve closure, and providing means for mounting the valve closure for movement between the valve seat, impeding flow through the passageway from the esophageal end, and positions away from the valve seat permitting flow through the passageway from the tracheal end.

Illustratively according to this aspect of the invention, providing in the cartridge a valve closure and providing means for mounting the valve closure for movement between the valve seat and positions away from the valve seat comprises unitarily forming the valve closure and the means for mounting the valve closure from a resilient elastomer.

Illustratively according to this aspect of the invention, providing means for mounting the valve closure for movement between the valve seat and positions away from the valve seat comprises providing an elastomeric ring, providing on the elastomeric ring an elastomeric hinge element extending away from the elastomeric ring and forming the valve closure on a second end of the elastomeric hinge element.

Illustratively according to this aspect of the invention, providing means for mounting the valve closure comprises providing on the cartridge a groove opening radially outwardly from an axis of the voice prosthesis for accommodating the elastomeric ring and providing on the cartridge a notch opening toward one of a tracheal end and an esophageal end of the cartridge for accommodating the elastomeric hinge element.

According to another aspect of the invention, a method of making a voice prosthesis device comprises providing a first passageway, inserting into the first passageway a valve mechanism for controlling flow through the first passageway, providing on the valve mechanism at least one second passageway that intersects a sidewall of the first passageway when the valve mechanism is inserted into the first passageway, and filling the second passageway with a material to fix the valve mechanism in the first passageway.

Illustratively according to this aspect of the invention, providing on the valve mechanism at least one second passageway that intersects a sidewall of the first passageway when the valve mechanism is inserted into the first passageway comprises providing on the valve mechanism at least one second passageway that extends generally across the first passageway from a sidewall of the first passageway to a sidewall of the first passageway when the valve mechanism is inserted into the first passageway.

Illustratively according to this aspect of the invention, providing on the valve mechanism at least one second passageway that extends generally across the first passageway from a sidewall of the first passageway to a sidewall of the first passageway when the valve mechanism is inserted into the first passageway comprises providing on the valve mechanism two second passageways that extend generally across the first passageway from a sidewall of the first passageway to a sidewall of the first passageway when the valve mechanism is inserted into the first passageway.

Illustratively according to this aspect of the invention, providing on the valve mechanism two second passageways that extend generally across the first passageway from a sidewall of the first passageway to a sidewall of the first passageway when the valve mechanism is inserted into the first passageway comprises providing on the valve mechanism two second passageways that extend generally parallel to each other across the first passageway from a sidewall of the first passageway to a sidewall of the first passageway when the valve mechanism is inserted into the first passageway.

Further illustratively according to this aspect of the invention, the method includes forming adjacent a tracheal end of the first passageway a tracheal flange and forming adjacent an esophageal end of the first passageway an esophageal flange.

Illustratively according to this aspect of the invention, inserting into the first passageway a valve mechanism comprises inserting into the first passageway a valve mechanism permitting flow through the first passageway from the tracheal end and impeding flow through the first passageway from the esophageal end.

According to another aspect of the invention, a voice prosthesis device for insertion into a tracheoesophageal opening of a wearer comprises a first passageway, a valve mechanism for inserting into the first passageway for controlling flow through the first passageway, at least one second passageway provided in the valve mechanism, the at least one second passageway intersecting a sidewall of the first passageway when the valve mechanism is inserted into the first passageway, and a material for placement in the second passageway to fix the valve mechanism in the first passageway.

Illustratively according to this aspect of the invention, the at least one second passageway that intersects a sidewall of the first passageway when the valve mechanism is inserted into the first passageway comprises at least one second passageway that extends generally across the first passageway from a sidewall of the first passageway to a sidewall of the first passageway when the valve mechanism is inserted into the first passageway.

Illustratively according to this aspect of the invention, the at least one second passageway that extends generally across the first passageway from a sidewall of the first passageway to a sidewall of the first passageway when the valve mechanism is inserted into the first passageway comprises two second passageways that extend generally across the first passageway from a sidewall of the first passageway to a sidewall of the first passageway when the valve mechanism is inserted into the first passageway.

Illustratively according to this aspect of the invention, the two second passageways that extend generally across the first passageway from a sidewall of the first passageway to a sidewall of the first passageway when the valve mechanism is inserted into the first passageway comprise two second passageways that extend generally parallel to each other across the first passageway from a sidewall of the first passageway to a sidewall of the first passageway when the valve mechanism is inserted into the first passageway.

Further illustratively according to this aspect of the invention, the voice prosthesis comprises a tracheal flange adjacent a tracheal end of the first passageway and an esophageal flange adjacent an esophageal end of the first passageway.

Illustratively according to this aspect of the invention, the valve mechanism for inserting into the first passageway for controlling flow through the first passageway comprises a valve mechanism permitting flow through the first passageway from the tracheal end and impeding flow through the first passageway from the esophageal end.

BRIEF DESCRIPTION OF THE DRAWINGS

The invention may best be understood by referring to the following detailed description and accompanying drawings which illustrate the invention. In the drawings.

DETAILED DESCRIPTIONS OF ILLUSTRATIVE EMBODIMENTS

Referring now to FIGS. 1-6, a voice prosthesis device 20 includes a generally right circular cylindrical barrel 22 having a tracheal flange 24 at a tracheal end thereof and an esophageal flange 26 at an esophageal end thereof. While the illustrated barrel 22 is generally right circular cylindrical, it is understood that the word "cylindrical," as used in this application, is used in the mathematical sense, that is, to describe the body defined by a line moving in a closed plane path always parallel to another line. When the closed plane path is a circle, the cylinder is a circular cylinder; when an ellipse, a elliptical cylinder, and so on. When the ends of the cylinder are perpendicular to its axis, the cylinder is called a right cylinder. The surface 27 of esophageal flange 26 facing away from barrel 22 is contoured as, and for the reasons, described in, WO 03/057082. The esophageal flange 26 is also somewhat "teardrop" shaped in elevation to aid in orienting device 20 properly during insertion and in maintaining its orientation once inserted. The barrel 22 illustratively is molded from 50-60 durometer silicone, such as, for example, NuSil Technology med-4960 silicone.

Figure 1:
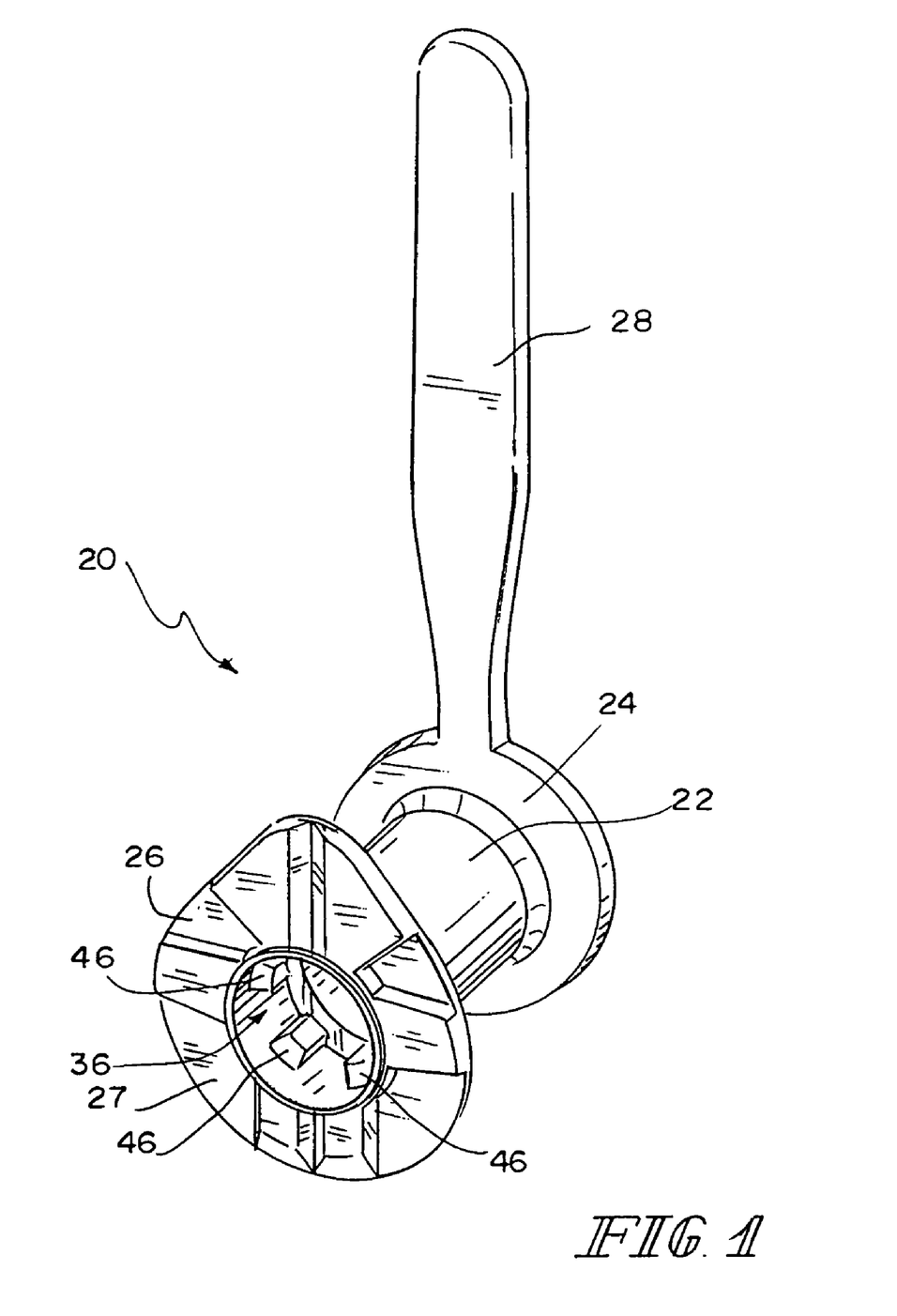
FIG. 1 illustrates a perspective view, from the esophageal end, of a voice prosthesis constructed according to the invention.
Figure 2:
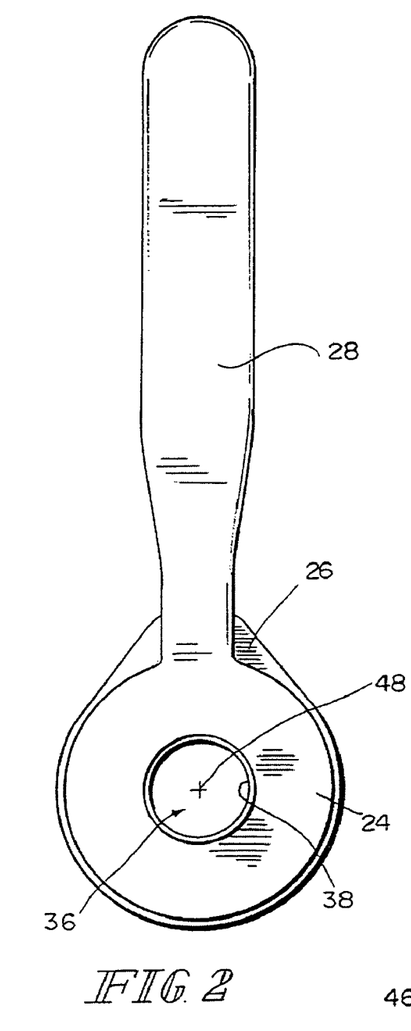
FIG. 2 illustrates a tracheal end elevational view of a component of the voice prosthesis illustrated in FIG. 1.
Figure 3:
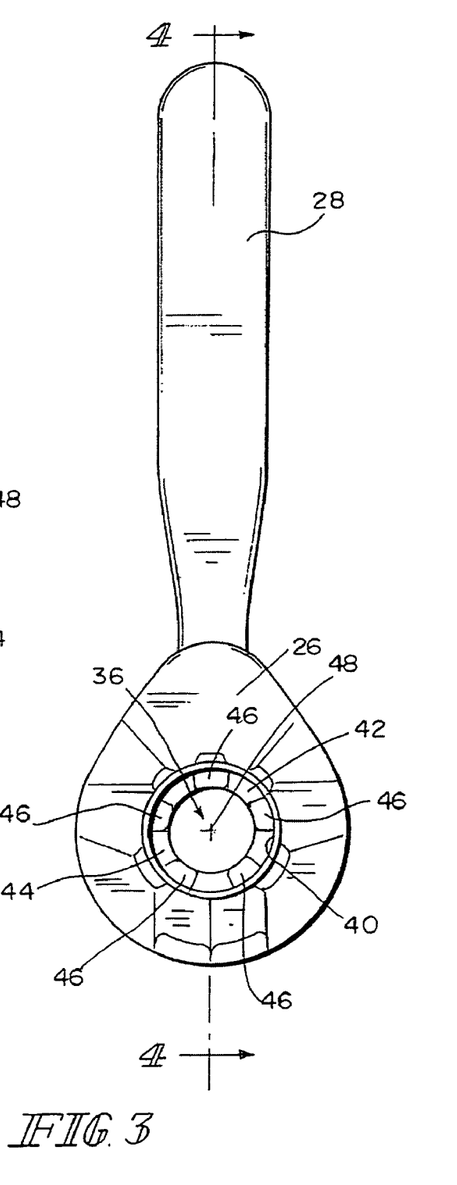
FIG. 3 illustrates an esophageal end elevational view of the component illustrated in FIG. 2.
Figure 4:
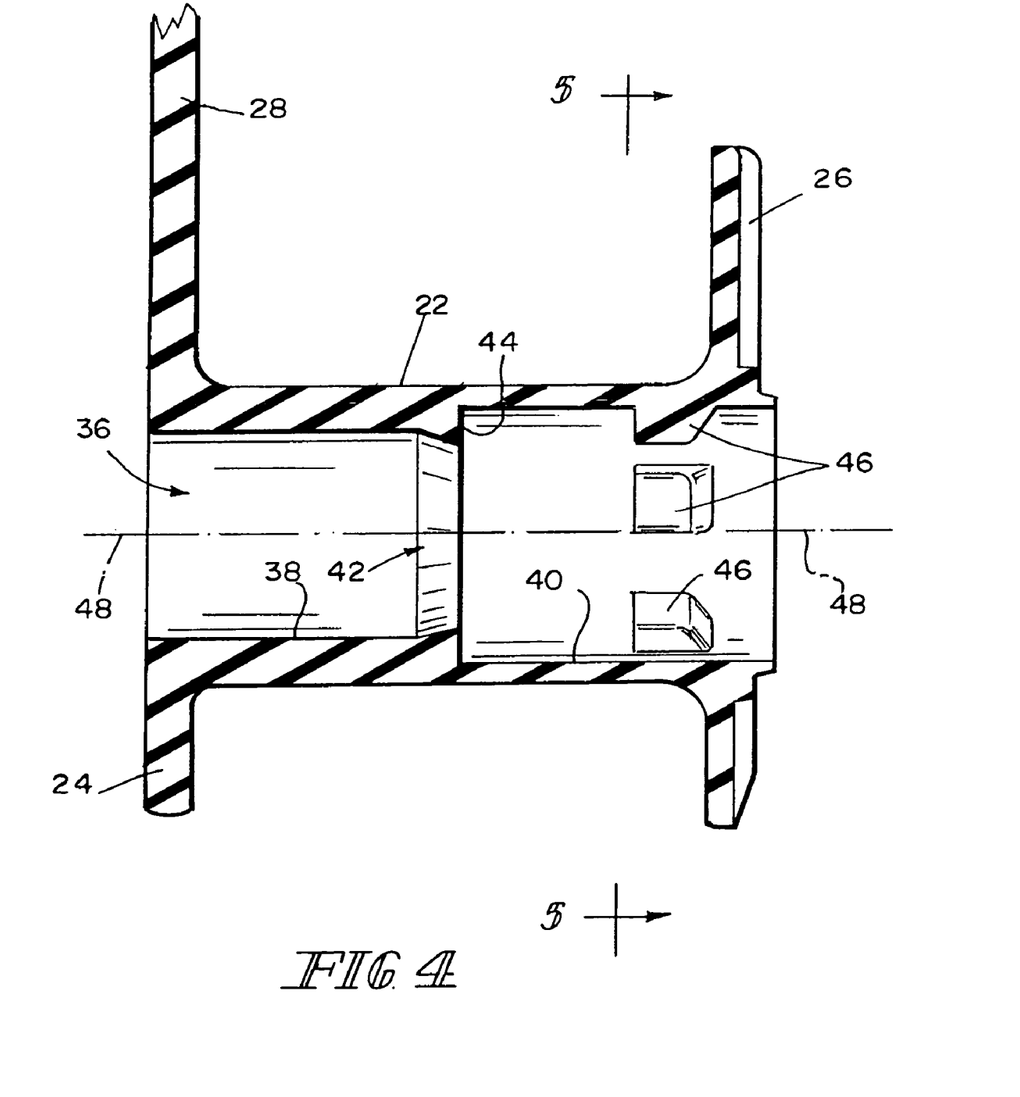
FIG. 4 illustrates an enlarged sectional view of the component illustrated in FIGS. 2-3, taken generally along section lines 4-4 of FIG. 3.
Figure 5:
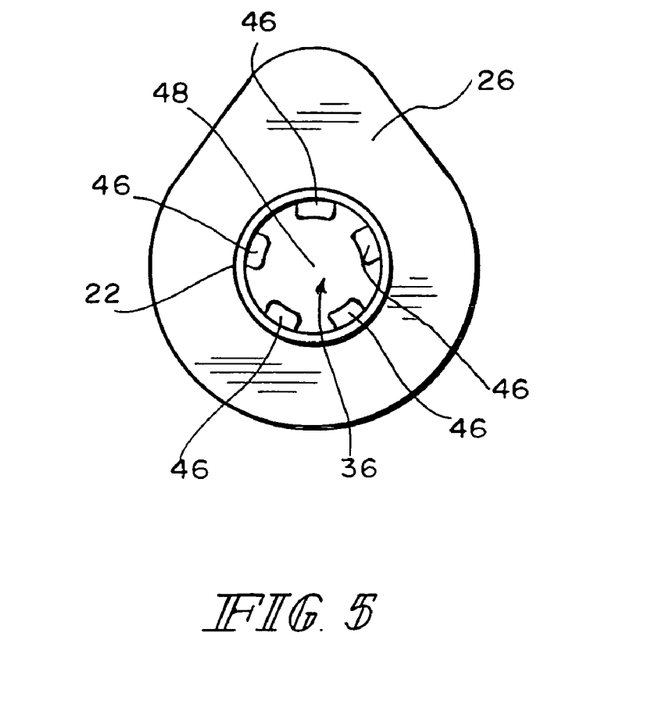
FIG. 5 illustrates a sectional view of the component illustrated in FIGS. 2-4, taken generally along section lines 5-5 of FIG. 4.
Figure 6:
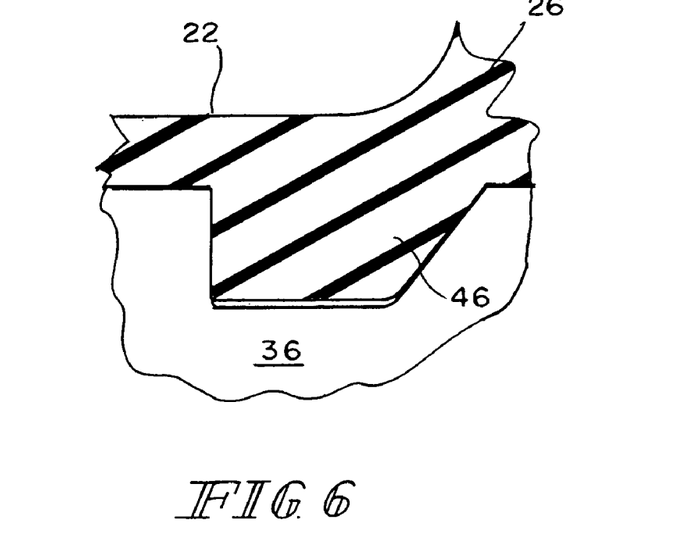
FIG. 6 illustrates an enlarged fragmentary sectional view of a detail of the component illustrated in FIGS. 2-5, taken generally along section lines 6-6 of FIG. 5.

As is customary of such devices 20, the tracheal flange 24 is provided with a strap 28 for fixing, for example, with adhesive tape, to the paratracheal skin 30 of the wearer 32. Additionally, the strap 28 may include attachment means for cooperating with attachment means on an insertion tool (not shown) with the aid of which the device 20 may be inserted into a tracheoesophageal puncture 34 of the wearer 32 to aid in the production of alaryngeal speech, all in accordance with well-known principles.

Barrel 22 includes a passageway 36 which in the illustrated embodiment is also generally right circular cylindrical. The inside diameter of sidewall 38 of the passageway 36 from the tracheal end 24 is slightly smaller. The inside diameter of the sidewall 40 of the passageway 36 from the esophageal end 26 is slightly larger. At a boundary 42 between diameters 38 and 40, the inside diameter tapers to a smaller diameter than the diameter of either sidewall 38 or sidewall 40, providing a radially inwardly extending stop 44. Between stop 44 and the esophageal end 26 of barrel 22, the inside diameter of barrel 22 is constant. A number, illustratively five, of somewhat right trapezoidal prism-shaped stops 46 project radially inwardly toward the axis 48 of device 20. The word "prism," as used in this application, is used in the mathematical sense, that is, to describe a solid figure whose bases or ends have the same size and shape and are parallel to one another, and each of whose sides is a parallelogram. Illustratively, stops 46 are perimetrally equally spaced at 72° intervals around sidewall 40.

Referring now to FIGS. 9-19, a cartridge 50 mounting a valve flap (or closure) 52 and a valve seat 54 is inserted from the tracheal end 24 into barrel 22. Cartridge 50 is pushed into barrel 22 past stops 46 and is captured between stops 46 and stop 44. The sloping sides of stops 46 aid in the insertion of cartridge 50 into barrel 22. Cartridge 50 includes a tracheal end 56 and an esophageal end 58. Esophageal end 58 is notched 60 along part of its perimeter to receive an elastomeric tab (or hinge) 62 by which elastomeric valve flap 52 is molded to projected inwardly toward the center of an elastomeric ring 64. Ring 64, tab 62 and valve flap 52 illustratively are molded as a single component from about 5 wt. % to about 11 wt. % silver oxide powder filled-NuSil Technology med-4960 silicone with a very small amount of an inhibitor, for example, 0.00043 wt. %, of 2-methy-3-butyn-2-ol. Ring 64 is received in a radially outwardly opening groove 66 provided on the outer surface of cartridge 50, with tab 62 oriented to extend through notch 60. Tab 62 and valve flap 52 are molded at an angle of, for example, 15° from perpendicular to the axis 48 of device 20 to be biased against seat 54 in the assembled device 20. A band or ring 68 of, for example, titanium, is slipped around cartridge 50 over ring 64 after cartridge 50 is assembled, and before cartridge 50 is inserted into barrel 22.

Figure 14:
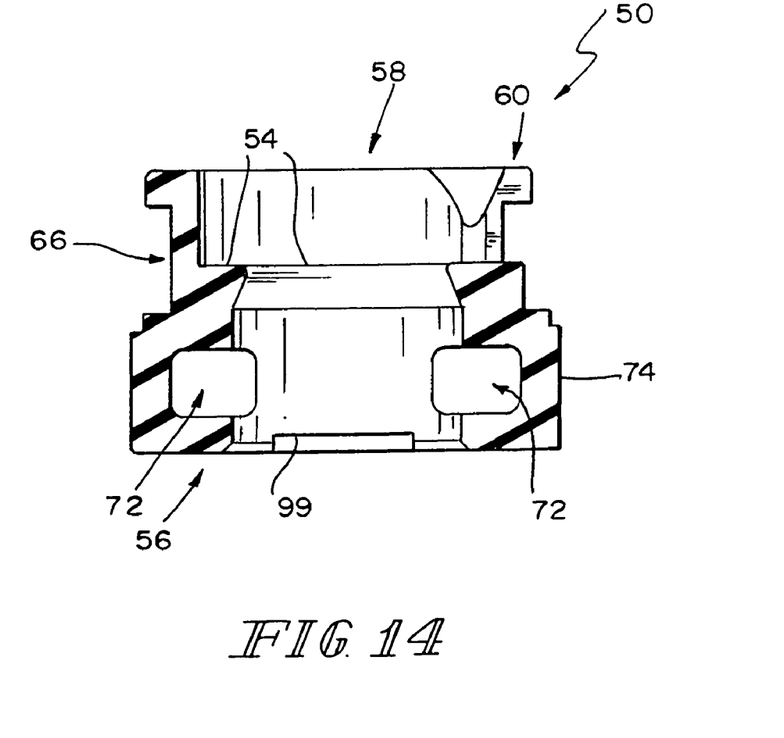
FIG. 14 illustrates a sectional view of the component illustrated in FIGS. 9-13, taken generally along section lines 14-14 of FIG. 13.
Figure 15:
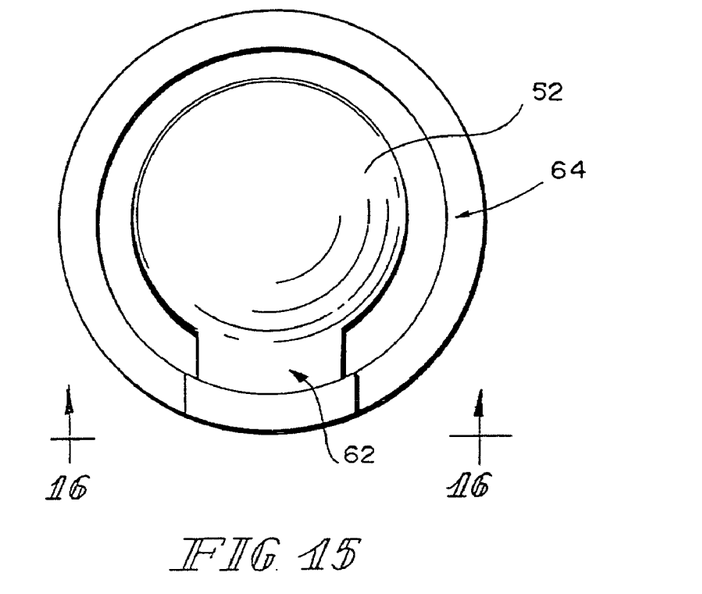
FIG. 15 illustrates an esophageal end elevational view of another component of a voice prosthesis constructed according to the invention.
Figure 16:
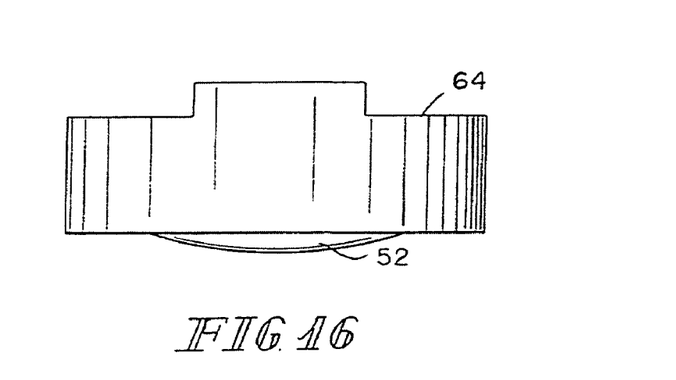
FIG. 16 illustrates an elevational view of the component illustrated in FIG. 15, taken generally along section lines 16-16 of FIG. 15.
Figure 17:
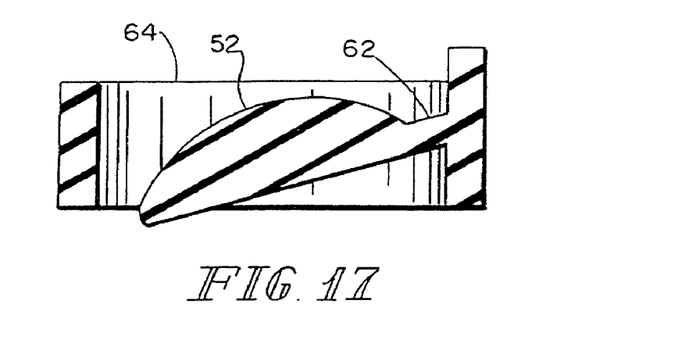
FIG. 17 illustrates a sectional view of the component illustrated in FIGS. 15-16, taken generally along section lines 17-17 of FIG. 15.
Figure 18:
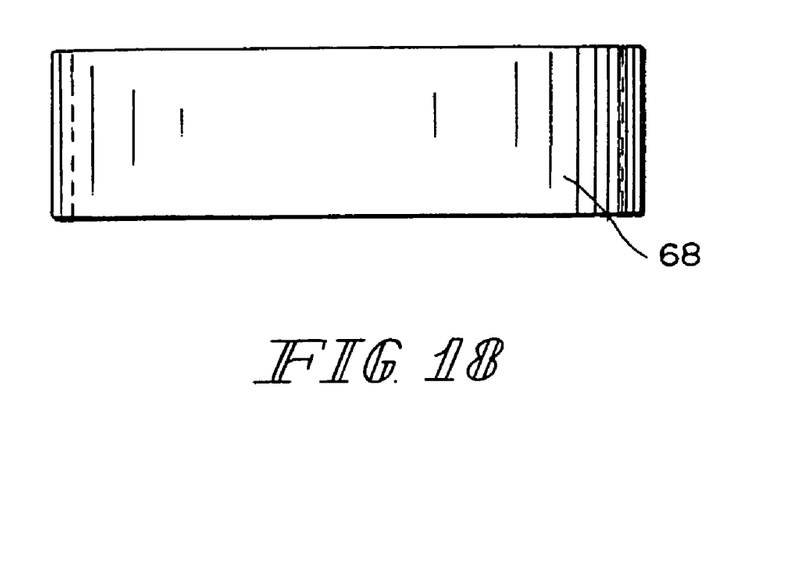
FIG. 18 illustrates a side elevational view of another component of a voice prosthesis constructed according to the invention.
Figure 19:
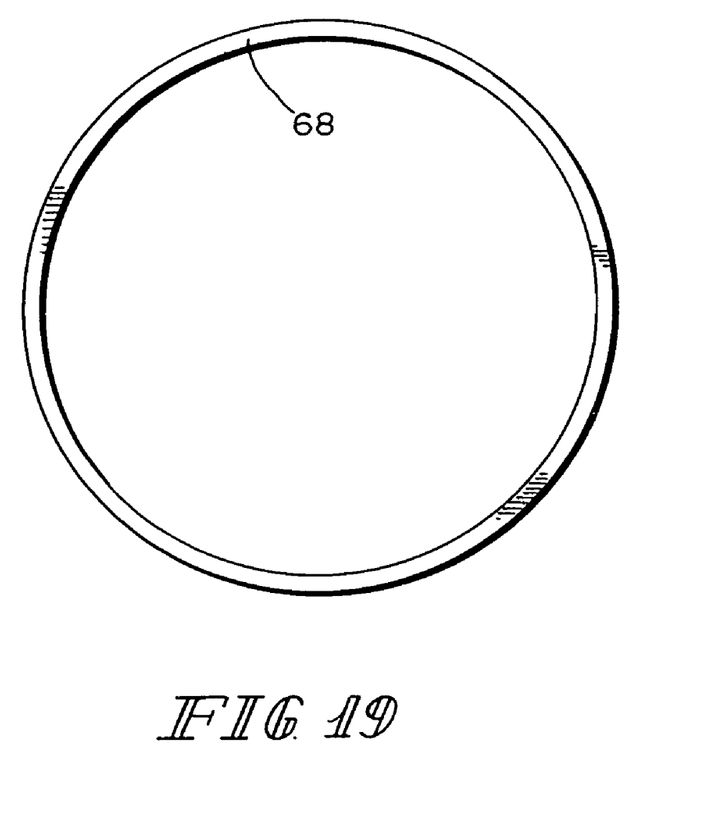
FIG. 19 illustrates an end elevational view of the component illustrated in FIG. 18.
Figure 20:
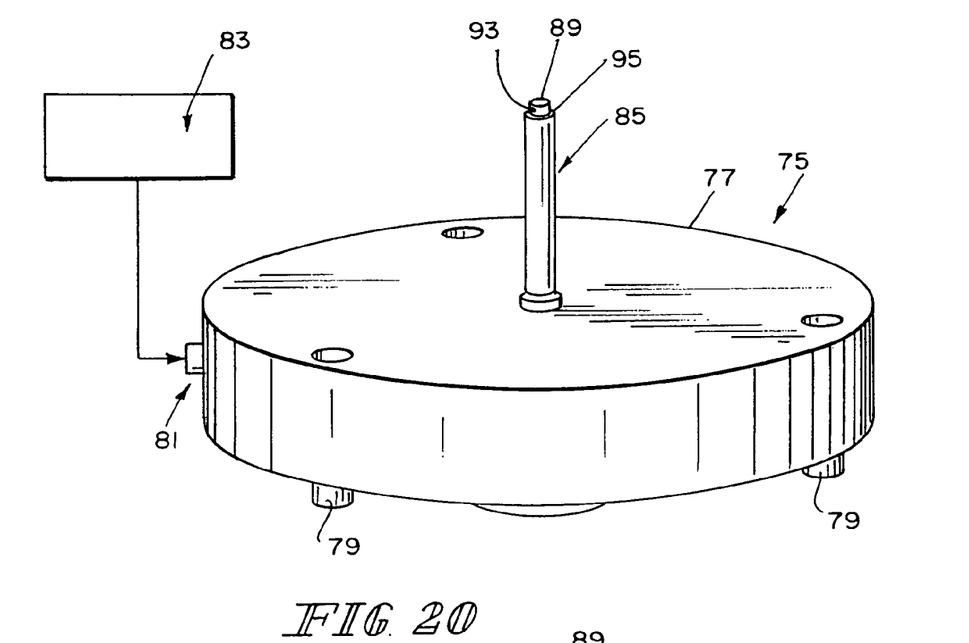
FIG. 20 illustrates a perspective view of a device useful in making devices according to an aspect of the invention.
Figure 21:
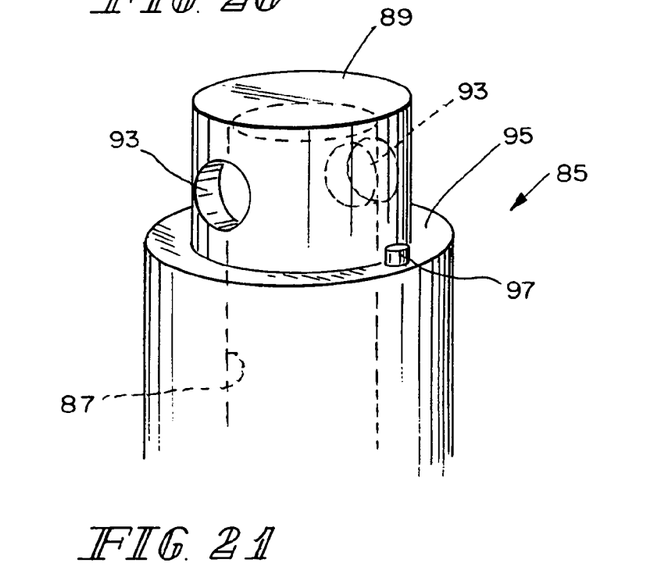
FIG. 21 illustrates an enlarged perspective view of a detail of the device illustrated in FIG. 20.

Cartridge 50 further includes two passageways 72 which extend generally across cartridge 50 and are defined between chords of the circular sidewall 74 which defines the outer dimension of cartridge 50 when viewed from an end thereof. Once cartridge 50 is assembled into barrel 22, an amount of a material, such as, for example, a room temperature curing silicone adhesive, sufficient to fill each passageway 72 is introduced, for example, by using a fixture 75 of the type illustrated in FIGS. 20-21. As best illustrated in FIG. 14, in the illustrated embodiment of the cartridge 50, the passageways 72 intersect the inside diameter of the cartridge 50, and thus are accessible through it. Fixture 75 includes a base 77 having adjustable legs 79 and a connector 81 for connecting it to a source 83 of the material which is to be injected into passageways 72. A needle 85 having a central passageway 87 communicating with connector 79 terminates adjacent a tip 89 of needle 85 in two diametrical openings 93 in needle 85. Needle 85 also includes a shoulder 95 against which the tracheal end of cartridge 50 rests, presenting openings 93 at the inner ends of the passageways 72. Passageways 72 are properly aligned in communication with openings 93 by cooperating features 97, 99 on needle 85 and cartridge 50, respectively. An amount of the material is then injected through openings 93 into passageways 72 sufficient to fill them. The material may also be injected using (a) needle(s) through sidewall 40 into passageways 72. However the material is introduced, as the material cures in contact with the inner sidewall 40, it works to secure the cartridge 50, and the valve flap 52 and valve seat 54 contained within it, in place in the barrel 22. Cartridge 50 illustratively is constructed from Kynar® 720 brand polyvinylidene fluoride (PVDF) or Estane® 58091 brand thermoplastic polyurethane (TPU). An illustrative room temperature curing silicone adhesive is NuSil Technology med-1511 room temperature vulcanizing (RTV) silicone adhesive.

Figure 7:
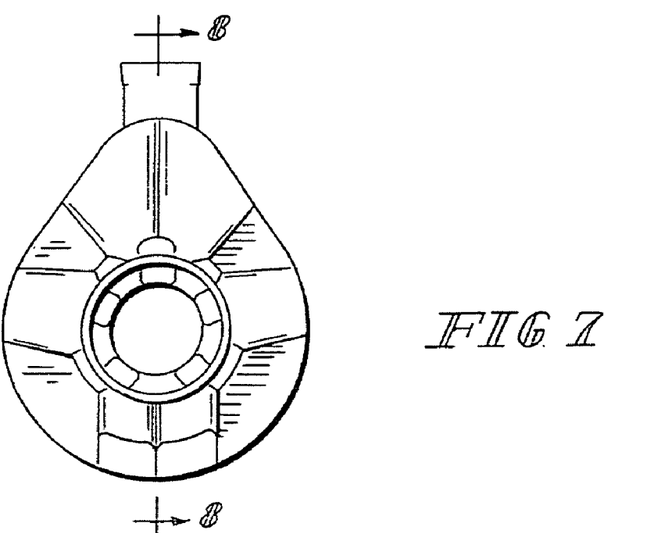
FIG. 7 illustrates an esophageal end elevational view of an alternative component to the component illustrated in FIGS. 2-5.
Figure 8:
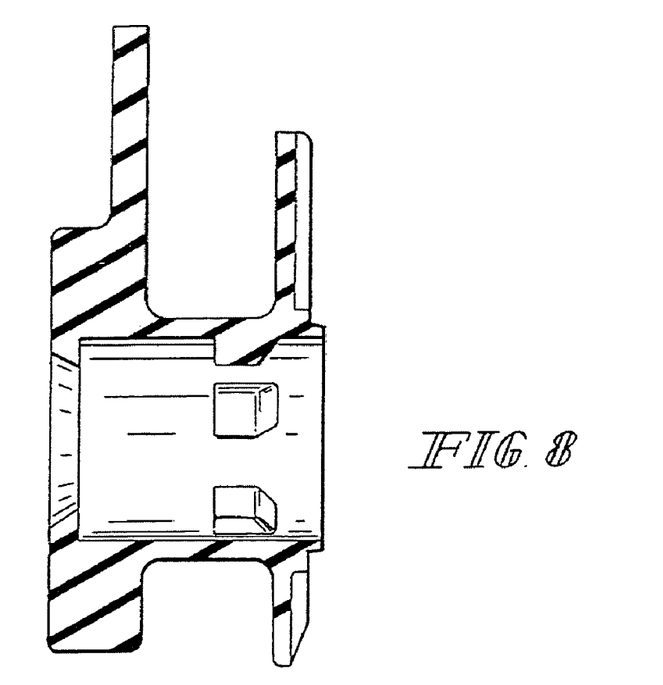
FIG. 8 illustrates a sectional view of the component illustrated in FIG. 7, taken generally along section lines 8-8 of FIG. 7.
Figure 9:
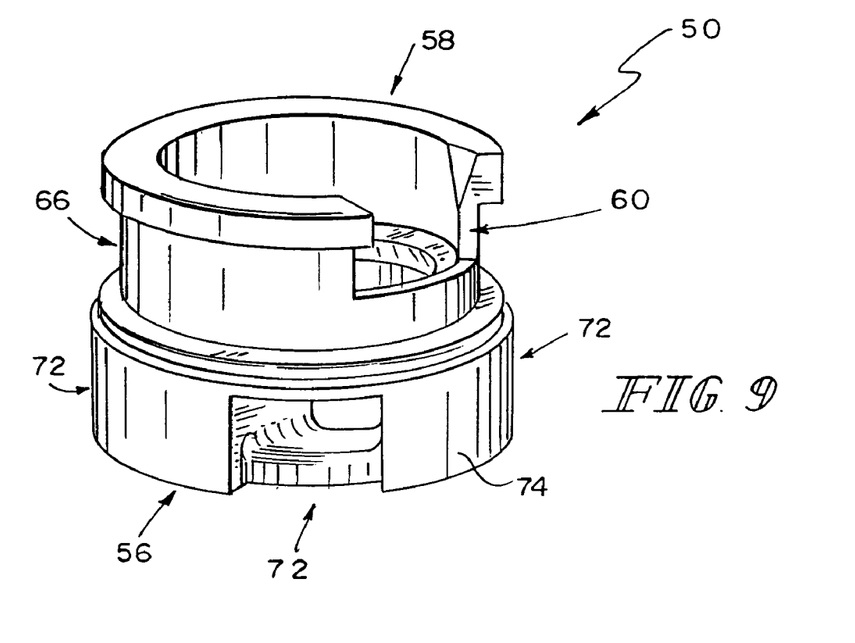
FIG. 9 illustrates a perspective view of another component of a voice prosthesis constructed according to the invention.
Figure 10:
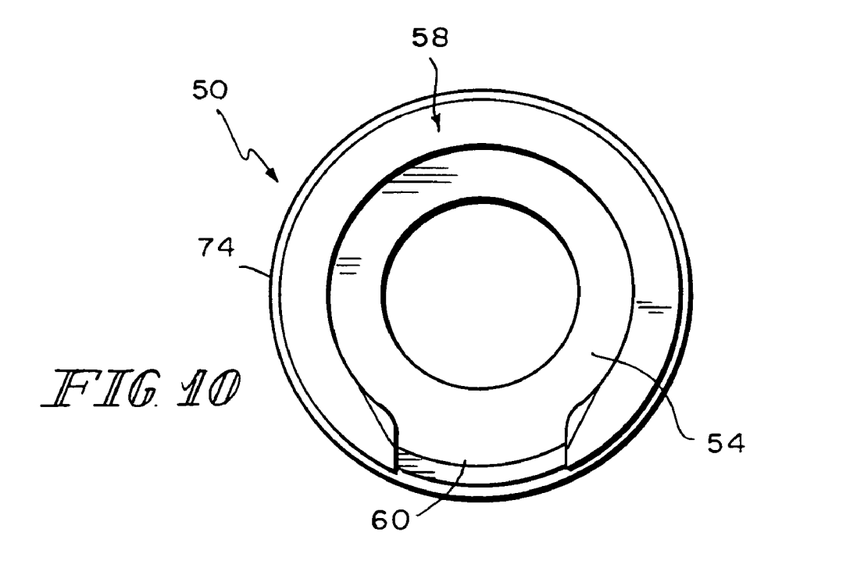
FIG. 10 illustrates an esophageal end elevational view of the component illustrated in FIG. 9.
Figure 11:
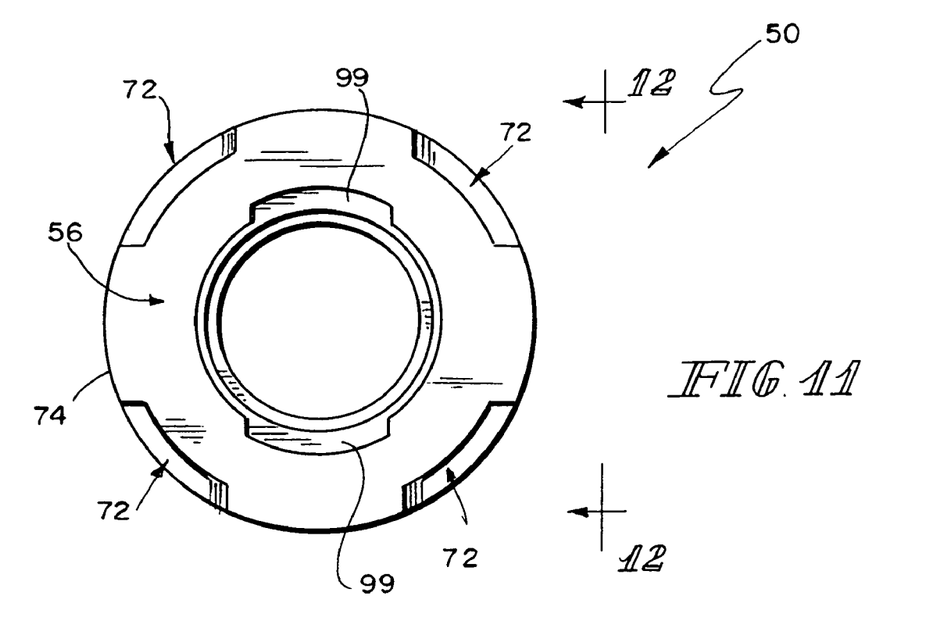
FIG. 11 illustrates a tracheal end elevational view of the component illustrated in FIGS. 9-10.
Figure 12:
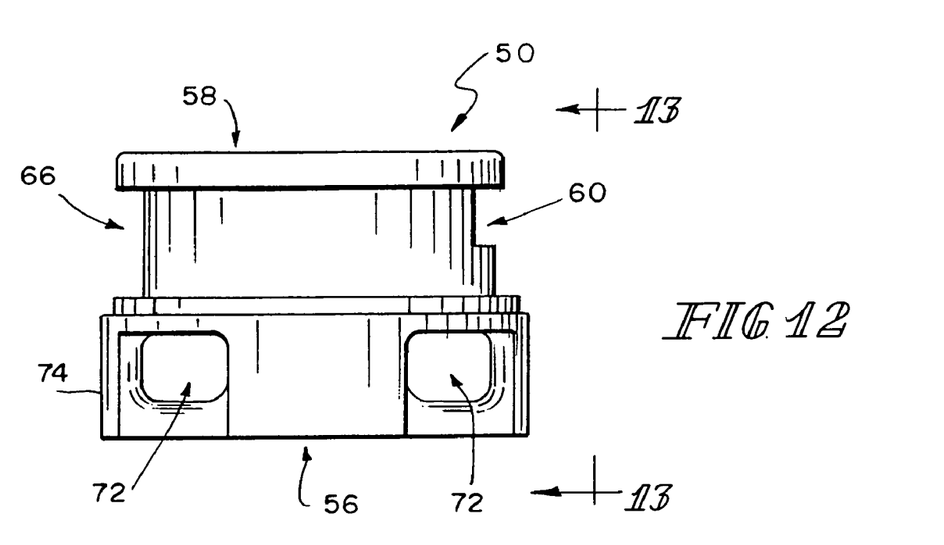
FIG. 12 illustrates an elevational view of the component illustrated in FIGS. 9-11, taken generally along section lines 12-12 of FIG. 11.
Figure 13:
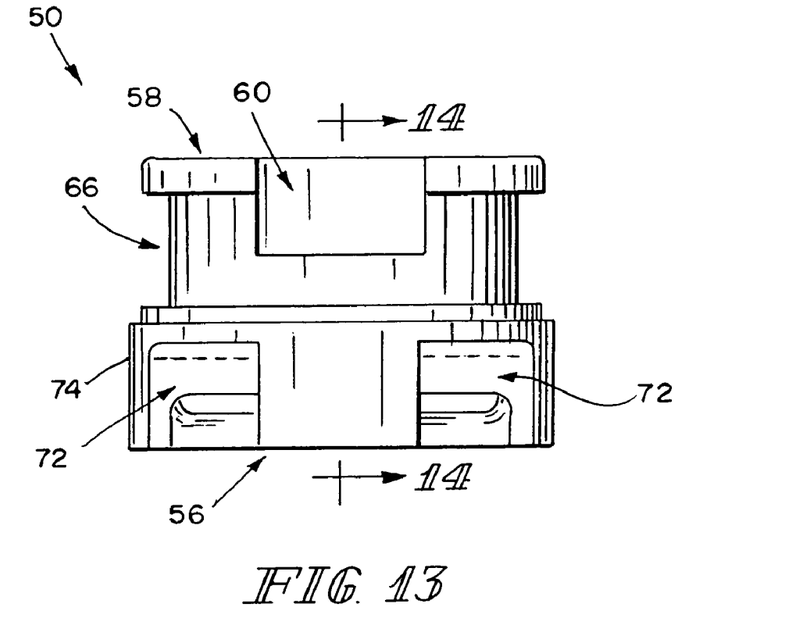
FIG. 13 illustrates an elevational view of the component illustrated in FIGS. 9-12, taken generally along section lines 13-13 of FIG. 12.

Referring now to FIGS. 7-8, in another embodiment, a barrel 122 includes a passageway 136 which in the illustrated embodiment is also generally right circular cylindrical. The inside diameter of sidewall 140 of the passageway 136 from the esophageal end 126 has as first dimension. From the tracheal end 124, the inside diameter tapers to a smaller diameter than the diameter of sidewall 140, providing a radially inwardly extending stop 144. Between stop 144 and the esophageal end 126 of barrel 122 the inside diameter of barrel 122 is constant. A number, again, illustratively five, of somewhat trapezoidal prism-shaped stops 146 project radially inwardly toward the axis 148 of device 120. Illustratively, stops 146 are perimetrally equally spaced at 72° intervals around sidewall 140. The region of barrel 122 between stop 144 and stops 146 is sized to accommodate the same cartridge 50 as the embodiment of FIGS. 1-6.

What is claimed is:

1. A voice prosthesis device for insertion into a tracheoesophageal opening of a wearer, the voice prosthesis device providing a passageway therethrough, a tracheal flange adjacent a tracheal end, and an esophageal flange adjacent an esophageal end, the tracheal flange and esophageal flange aiding in retaining the voice prosthesis device in the tracheoesophageal opening, the passageway including a first stop extending inwardly from a sidewall of the passageway into a lumen of the passageway between the tracheal and esophageal ends, and a plurality of second stops extending inwardly from the sidewall of the passageway into the lumen of the passageway between the first stop and the esophageal end of the passageway, and a valve mechanism permitting flow through the passageway from the tracheal end and impeding flow through the passageway from the esophageal end.

2. The voice prosthesis device of claim 1 wherein the passageway includes an axis about which it is generally symmetric, the second stops extending generally radially inwardly from the sidewall toward the axis.

3. The voice prosthesis device of claim 2 wherein the second stops are perimetrally substantially uniformly spaced about the sidewall.

4. The voice prosthesis device of claim 1 wherein the passageway adjacent the tracheal end of the passageway has a smaller transverse dimension than a transverse dimension of the passageway adjacent the esophageal end thereof.

5. The voice prosthesis device of claim 4 wherein the first stop is provided between the sidewall adjacent the tracheal end of the passageway and the sidewall adjacent the esophageal end of the passageway.

6. The voice prosthesis device of claim 1 wherein the first stop is provided adjacent the tracheal end of the passageway.

7. The voice prosthesis device of claim 1 wherein the valve mechanism comprises a cartridge providing a valve seat, a valve closure, and means for mounting the valve closure for movement between the valve seat and positions away from the valve seat.

8. The voice prosthesis device of claim 7 wherein the cartridge is secured within the passageway axially between the first stop and the plurality of second stops.

9. The voice prosthesis device of claim 7 wherein the valve closure and the means for mounting the valve closure are unitarily formed from a resilient elastomer.

10. The voice prosthesis device of claim 9 wherein the means for mounting the valve closure comprises an elastomeric ring and an elastomeric hinge element having a first end formed on the elastomeric ring, the valve closure formed on a second end of the elastomeric hinge element.

11. The voice prosthesis device of claim 10 wherein the cartridge comprises a groove opening radially outwardly from an axis of the voice prosthesis for accommodating the elastomeric ring and a notch opening toward one of a tracheal end and an esophageal end of the cartridge for accommodating the elastomeric hinge element.

12. The voice prosthesis device of claim 11 wherein the notch opens toward the esophageal end of the cartridge.

13. The voice prosthesis device of claim 9 wherein the resilient elastomer further comprises an antimicrobial.

14. The voice prosthesis device of claim 13 wherein the antimicrobial comprises a metal atom or ion.

15. The voice prosthesis device of claim 14 wherein the antimicrobial comprises silver oxide powder.

16. A voice prosthesis device for insertion into a tracheoesophageal opening of a wearer, the voice prosthesis device comprising:
    a barrel defining a passageway having first and second stops extending radially inward therefrom into a lumen of the passageway, the barrel including a tracheal end and an esophageal end axially spaced from one another, the first stop located axially between the tracheal and esophageal ends and the second stop located axially between the first stop and the esophageal end;
    a tracheal flange extending from the tracheal end;
    an esophageal flange extending from the esophageal end, the tracheal and esophageal flanges aiding in retaining the voice prosthesis in the tracheoesophageal opening; and
    a valve mechanism secured axially within the passageway by the first and second stops, the valve mechanism permitting flow through the passageway from the tracheal end and impeding flow through the passageway from the esophageal end.

17. The voice prosthesis device of claim 16 wherein the valve mechanism is secured axially between the first and second stops.

18. The voice prosthesis device of claim 16 wherein the valve mechanism includes a cartridge housing a valve member displaceable between open and closed positions, the cartridge including a recessed outer surface receiving the second stop therein.

19. The voice prosthesis device of claim 16 wherein the second stop includes a sloped surface increasing in diameter in a direction from the esophageal end to the tracheal end.

* * * * *